US012721647B2

(12) United States Patent
Hu et al.

(10) Patent No.: US 12,721,647 B2
(45) **Date of Patent: *Sep. 1, 2026**

(54) PUNCTURE INSTRUMENT

(71) Applicant: BEIJING MEDIS MEDICAL TECHNOLOGY CO., LTD., Beijing (CN)

(72) Inventors: Meng Hu, Beijing (CN); Dong Guo, Beijing (CN)

(73) Assignee: BEIJING MEDIS MEDICAL TECHNOLOGY CO., LTD., Beijing (CN)

( * ) Notice: Subject to any disclaimer, the term of this patent is extended or adjusted under 35 U.S.C. 154(b) by 292 days.

This patent is subject to a terminal disclaimer.

(21) Appl. No.: 18/293,675

(22) PCT Filed: Jul. 29, 2022

(86) PCT No.: PCT/CN2022/108990
§ 371 (c)(1),
(2) Date: Jul. 5, 2024

(87) PCT Pub. No.: WO2023/006075
PCT Pub. Date: Feb. 2, 2023

(65) Prior Publication Data

US 2024/0415536 A1 Dec. 19, 2024

(30) Foreign Application Priority Data

Jul. 30, 2021 (CN) ......................... 202110869345.0

(51) Int. Cl.
*A61B 17/34* (2006.01)
*A61B 34/20* (2016.01)

(52) U.S. Cl.
CPC .. *A61B 17/3403* (2013.01); *A61B 2017/3413* (2013.01); *A61B 17/3415* (2013.01)

(58) Field of Classification Search
CPC ...... A61M 2005/1585; A61M 25/0606; A61M 25/06; A61M 25/0021; A61M 25/0043;
(Continued)

(56) References Cited

U.S. PATENT DOCUMENTS 8,632,468 B2 1/2014 Glossop et al.
2007/0021767 A1* 1/2007 Breznock ......... A61B 17/00234 606/185

(Continued)

FOREIGN PATENT DOCUMENTS

CN 102395327 A 3/2012
CN 202277348 U * 6/2012

(Continued)

OTHER PUBLICATIONS

European Patent Office, "Extended European Search Report", issued in connection with EP Patent Application No. 22848679.1 on Feb. 17, 2025, 8 pages.

(Continued)

*Primary Examiner* — Katherine M Shi
(74) *Attorney, Agent, or Firm* — Hanley, Flight & Zimmerman, LLC

(57) ABSTRACT

The present disclosure relates to a puncture system, which can be applied to a puncture operation with electromagnetic combined with ultrasound navigation to achieve a safe, precise, efficient and easy-to-operate puncture procedure.

18 Claims, 11 Drawing Sheets

(58) Field of Classification Search
CPC ........ A61M 25/065; A61M 2025/0681; A61M 25/0662; A61B 10/0233; A61B 5/062; A61B 5/6849; A61B 5/6848; A61B 17/3496; A61B 17/34; A61B 17/3474; A61B 2017/3454; A61B 17/3478; A61B 2017/00252; A61B 17/3415; A61B 17/3417; A61B 17/3421; A61B 17/3403; A61B 2017/3413; A61B 2034/107; A61B 34/20; A61B 2034/2051; A61B 2034/2063; A61B 2034/2065; A61B 8/0841; A61B 8/085; A61B 8/4254; A61B 8/445; A61B 8/5207; A61B 8/0891
See application file for complete search history.

(56) References Cited

U.S. PATENT DOCUMENTS

| | | | | |
|---|---|---|---|---|
| 2010/0217117 | A1 | 8/2010 | Glossop et al. | |
| 2011/0130750 | A1 * | 6/2011 | Ormsby | A61B 18/1815 606/33 |
| 2012/0016316 | A1 | 1/2012 | Zhuang et al. | |
| 2015/0258270 | A1 * | 9/2015 | Kunis | A61M 5/00 604/506 |
| 2020/0029856 | A1 * | 1/2020 | Sharareh | A61B 5/0084 |

FOREIGN PATENT DOCUMENTS

| | | | | |
|---|---|---|---|---|
| CN | 109009425 A | * | 12/2018 | A61B 18/1815 |
| CN | 109259827 A | | 1/2019 | |
| CN | 209004071 U | | 6/2019 | |
| CN | 113456189 A | | 10/2021 | |
| CN | 113456191 A | | 10/2021 | |
| CN | 113456990 A | | 10/2021 | |
| CN | 216876522 U | | 7/2022 | |
| CN | 216876523 U | | 7/2022 | |
| EP | 4378405 A1 | | 6/2024 | |
| EP | 4378412 A1 | | 6/2024 | |
| JP | 2017510347 A | * | 4/2017 | A61B 5/14532 |

OTHER PUBLICATIONS

China National Intellectual Property Administration, "First Notification of Office Action," issued in connection with Chinese Patent Application No. 202110869345.0, dated Aug. 10, 2024, 7 pages. [English translation provided].

China National Intellectual Property Administration, "First Search Report," issued in connection with Chinese Patent Application No. 202110869345.0, dated Aug. 10, 2024, 4 pages. [English translation provided].

International Searching Authority, "International Search Report," issued in connection with International Application No. PCT/CN2022/108990, dated Oct. 28, 2022, 7 pages. [English translation provided].

International Searching Authority, "Written Opinion," issued in connection with International Application No. PCT/CN2022/108990, dated Oct. 28, 2022, 12 pages. [English translation provided].

International Bureau, "International Preliminary Report on Patentability," issued in connection with International Application No. PCT/CN2022/108990, dated Jan. 18, 2024, 13 pages. [English translation of Written Opinion provided].

* cited by examiner 1321
132

PUNCTURE INSTRUMENT

CROSS-REFERENCE TO RELATED APPLICATIONS

This patent arises from a U.S. National Stage of International Application No. PCT/CN2022/108990 filed on Jul. 29, 2022, which claims priority to Chinese Patent Application No. 202110869345.0 which was filed on Jul. 30, 2021. International Application No. PCT/CN2022/108990 and Chinese Patent Application No. 202110869345.0 are both hereby incorporated herein by reference in their entireties.

TECHNICAL FIELD

The present disclosure relates to the technical field of medical devices, and in particular to a puncture instrument.

BACKGROUND

Hereinafter the relevant background art of the present disclosure is illustrated, but these illustrations do not necessarily constitute the prior art of the present disclosure.

Interventional Radiology is a marginal discipline that developed rapidly in the late 1970s. It includes a series of techniques of diagnosis and treatment of various diseases by using instruments such as catheters, guide wires and the like under the guidance of medical imaging equipment, based on image diagnostics and clinical diagnostics, and combined with the principle of clinical therapeutics. That is, it is a discipline that a specially-made catheter or instrument is inserted into a site of lesion for diagnostic imaging and treatment by a transdermal puncture approach or original orifices of the human body under the guidance of imaging medicine (X-ray, ultrasound, CT (Computed Tomography), MRI (Magnetic Resonance Imaging)), or the tissues are collected for examinations of the cytology, the bacteriology and the biochemistry.

Interventional radiology provides new drug delivery route and surgical method for modern medical diagnosis and treatment. Compared with traditional drug delivery routes and surgical methods, the interventional radiology is more direct, effective, simple and microtraumatic. The interventional radiology has opened up a new way of treatment, and it is simple, safe, with less trauma, with fewer complications, quick effect, and microtraumatic; has strong repeatability, accurate positioning, high curative effect and quick effect; has a low comorbidity rate. The application of various technologies is simple and easy.

The interventional radiology may be divided into interventional diagnosis and interventional therapy according to the purpose; and may be divided into vascular interventional radiology (drug perfusion; embolization technique; angioplasty and stenting; filter technology, etc.) and non-vascular radiological interventionology (puncture biopsy; drainage technology; removal of foreign bodies; lumen stent, etc.) according to the technology; and may be divided into tumor interventional radiology, non-tumor interventional radiology, neurointerventional radiology and so on according to the scope of clinical application.

Medical imaging equipment used in the interventional radiology mainly includes X-ray, ultrasound, CT, MRI, etc., among which, X-ray and CT have radioactivity, but MRI has to be applied in conjunction with non-ferromagnetic devices and environments. For intraoperative interventional guidance, multiple number of times of imaging and long-time imaging is required, harm to patients and health care workers caused by the radioactivity of X-ray and CT as well as the non-ferromagnetic requirement of MRI for supporting equipment and environment both of which cause inconvenience and difficulty for interventional diagnosis and treatment, which hinders the clinical application of interventional radiology.

Ultrasound has the characteristics of real-time imaging and no radioactivity and thus has been widely used in interventional radiology. However, the non-intuitive two-dimensional nature of ultrasonic imaging, and the coplanar nature of an ultrasonic imaging plane and an interventional tool and other similar problems may easily lead to difficulties and mistakes in positioning and guiding the interventional tool, and in turn lead to puncture errors, trauma, complications and other conditions, which thus requires the medical staff for executing intervention diagnosis and treatment to have a large amount of training, skillful technique and rich experience.

Ultrasonic interventional navigation is an important means of interventional radiology, which can display the movement of the interventional tool in the tissue in real time and provide a basis for selection of an interventional path. However, conventional ultrasound-guided intervention relies heavily on the operator's skill, experience and ultrasonic instrument performance, and may have problems such as many times of intervention and long operation time and the like, which may lead to an increased incidence of complications.

Due to the characteristics of ultrasonic imaging, in order to perform real-time imaging navigation of interventional instruments during the interventional process, it is necessary to keep the target, interventional instrument and ultrasonic imaging plane in the same plane. Due to the small tissue density, displacement/deformation is easy to happen under pressure, it necessary to readjust the angle of the ultrasonic probe and strength of pressing at any time according to the situation, and often the position of the corresponding interventional instrument will also change, then it is necessary to adjust the ultrasonic probe and the interventional instrument at the same time to re-image navigation, which is very difficult and has very high requirements for doctors.

Due to the volume effect of ultrasound, the imaging of the interventional instrument by ultrasonic equipment cannot reflect its true position and size, thus affecting the accuracy of navigation.

Currently, there is an electromagnetic positioning technique which uses electromagnetic induction to measure the position and direction of an object based on the Biot-Savart rule, in which a magnetic field signal sender generates a signal field by sending a magnetic field signal, and a magnetic signal receiving sensor receives the magnetic field signal and transmits the magnetic field signal to a magnetic field signal controller to obtain space vector information (space coordinates and direction) of the object.

The interventional instrument may be navigated by the electromagnetic positioning technique, the precision of which can effectively solve the problem of inaccurate interventional navigation caused by the volume effect of the ultrasonic imaging device.

Interventional radiology has a wide range of clinical applications, which may be applied to vascular diseases (such as vascular stenosis, portal hypertension, etc.), heart diseases (mitral stenosis, coronary artery stenosis, etc.), tumors (tumor blood supply artery infusion chemotherapy, embolization treatment of malignant tumors, etc.), non-vascular diseases (digestive tract, urinary tract, biliary tract, airway, stenosis of naso-lacrimal duct, etc.), puncture biopsy, etc.

Among them, the interventional diagnosis and treatment in which the intervention pathway is long and tortuous, and passes through important tissues and organs, such as transjugular intrahepatic portosystemic shunt (TIPS), has a high degree of difficulty, a high risk factor and high skill requirements, and in particular needs accurate and effective navigation techniques.

TIPS derives from the fact that the portal vein is often punctured during transjugular vein cholangiography and transhepatic biopsy, and is developed by renowned interventional radiologist Rosch J and his colleagues. By establishing a shunt inside the liver parenchyma between the hepatic vein and the portal vein, the portal vein resistance can be significantly reduced structurally in a microtraumatic manner, and this is one of the key measures to reduce portal vein pressure in patients with cirrhosis.

Since the first truly clinically significant TIPS with metal stent was performed in January 1988, through continuous improvement, at present, TIPS has been widely used in the treatment of esophageal and gastric varices rupture and bleeding, intractable hydrothorax and ascites, Budd-Chiari syndrome (BCS) and liver sinusoidal obstruction syndrome and the like caused by portal hypertension in cirrhosis (De Franchis, R. and V. I. F. Baveno, Expanding consensus in portal hypertension: Report of the Baveno VI Consensus Workshop: Stratifying risk and individualizing care for portal hypertension. J Hepartol, 2015.63(3):p. 743-52) (Chinese Medical Doctor Association Branch of Interventional Physicians. Chinese College of Interventionalists (CCI) clinical practice guidelines: management of TIPS for portal hypertension [J]. Chinese Journal of Hepatology, 2018,27 (8): 582-593).

The operation process of TIPS technology is as follows: 1) anesthesia; 2) portal vein imaging; 3) internal jugular vein puncture; 4) hepatic vein intubation; 5) portal vein puncture; 6) portal cavity channel establishment; 7) balloon catheter dilation and endoluminal stent implantation; 8) measurement and optimal threshold of PPG postoperatively; 9) embolization of portal collateral vessels.

Indications for TIPS include: 1) acute esophageal varix and bleed; 2) gastric varix and bleed; 3) preventing esophageal varix and bleed; 4) preventing gastric varix and bleed; 5) cirrhotic recalcitrant or recurrent ascites; hepatic pleural fluid and hepatorenal syndrome; 6) BCS (Budd-Chiari syndrome); 7) hepatic sinus obstruction syndrome; 8) portal hypertension complicated with portal vein thrombosis;

Contraindications for TIPS include:

1. Absolute contraindications: (1) congestive heart failure or severe valvular cardiac insufficiency; (2) uncontrollable systemic infection or inflammation; (3) Child-Pugh score >13 or end-stage liver disease score >18; (4) severe pulmonary hypertension; (5) severe renal insufficiency (except hepatogenic renal insufficiency); (6) rapidly progressive liver failure; (7) diffuse malignant tumor of liver; (8) contrast agent hypersensitivity.
2. Relative contraindications: (1) congenital cystic dilatation of intrahepatic bile duct (Caroli disease), obstructive dilatation of bile duct; (2) polycystic liver disease; (3) cavernous transformation of the portal vein; (4) moderate pulmonary hypertension; (5) severe or refractory HE (hepatic encephalopathy); (6) bilirubin >51.3 μmol/L (except cholestatic cirrhosis); (7) severe coagulation disease.

At present, there are three main technical difficulties in TIPS: 1) The success rate of portal vein puncture is low under X-ray monitoring; 2) Postoperative portal shunt channel restenosis; 3) The incidence of postoperative hepatic encephalopathy (HE) is high.

At present, with the use of PTFE (Polytetrafluoroethylene) coated stents (Perarnau J M, Le Gouge A, Nicolas C, et al. Covered vs. uncovered stents for transjugular intrahepatic portosystemic shunt: a randomized controlledtrial [J]. J Hepatol, 2014,60(5):962-968.DOI:10.1016/j.jhep.2014.01.015.) and special ePTFE (expended polytetrafluoroethylene) coated stents (Charon. J P, Alaeddin F H, Pimpalwar S A, et al. Results of aretrospective muhicenter trial of the Viatorr expanded Polyetrafluoroethylene covered stent—graft for transjugular intrahepatic portosystemic shunt creation [J]. JVIR (Journal of Vascular and Interventional Radiology), 2004, 15: 1219. 1230.), the shunt stenosis rate of subjects has been significantly reduced. The incidence of HE after TIPS is 18% to 45%. A retrospective clinical study on the establishment of shunt channels at the position of left branch of portal vein finds that the incidence of HE can be reduced to a certain extent (Zhu Qingliang, Deng Mingming, Tang Shixiao, et al. Effect of different stent positions on the incidence of hepatic encephalopathy after TIPS. Contemporary Medicine, 2016, 22 (4): 92-93.), and clinical studies on the selection of stents with smaller diameters and intrastent flow restriction finds that the incidence of HE is reduced to a certain extent and the symptoms of most patients with HE are improved (Riggio, O. et al. J Hepatol, 2010, 53 (2): p. 267-72) (Chinese Medical Doctor Association Branch of Interventional Physicians. Chinese clinical practice guidelines for portal hypertension transjugular intrahepatic portal shunt [J]. Chinese Journal of Hepatology, 2018,27 (8): 582-593).

In the process of transhepatic vein puncture of the portal vein during TIPS, the complications related to the technique mainly include biliary tract bleeding and injury, abdominal hemorrhage, hepatic artery injury, bile peritonitis, skin radiation burn and hematoma at the puncture site (Dariushina S R, Haskal Z J, Midia M, et al. Quality improvement guidelines for transjugular intrahepatic portosystemic shunts. J Vasc Interv Radiol 2016;27 (1): 1-7.). Although the incidence of these complications can be further reduced with the promotion of TIPS technology and the accumulation of operator experience, transhepatic vein puncture of the portal vein is still the biggest technical difficulty during TIPS surgery, the key step for the success or failure of TIPS, and the operation link that is prone to serious complications (Chinese Medical Doctor Association Branch of Interventional Physicians. Chinese clinical practice guidelines for portal hypertension transjugular intrahepatic portal shunt [J]. Chinese Journal of Hepatology, 2018,27 (8): 582-593).

The general procedure of transhepatic vein puncture of the portal vein is as follows: the operator estimates the puncture angle by observing imaging data before surgery; the patient underwent local anesthesia in the catheter room or the operating room; first, puncturing the right internal jugular vein; sending the catheter from the right internal jugular vein, through the right atrium and inferior vena cava to the right internal hepatic vein with the aid of X-ray fluoroscopy; performing the portal vein cuneiform angiography to clarify the structure of the portal vein and its branch anatomy; and puncturing the portal vein from the right hepatic vein forward and down.

This is currently considered the safest puncture route for TIPS surgery (Siramolpiwat, S., World J Gastroenterol, 2014. 20 (45): p. 16996-7010). At present, the main instruments for puncturing intrahepatic portal vein branches during TIPS surgery are RUPS-100 produced by Cook in the United States, and other similar instruments have basically disappeared. The RUPS-100 puncture assembly consists of an outer sheath, an expander, a plastic guide tube, a metal guide tube, a plastic sleeve and a puncture needle (Chu Jianguo, Development status and standardization of transjugular intrahepatic portal shunt technique in China, Chinese Electronic Journal of Interventional Radiology, 2013, 1 (2)).

However, the puncture assembly is designed according to the body type and vascular network characteristics of the European and American race, and it is not fully suitable for the body type of Asians and Chinese patients with liver atrophy mainly from hepatitis B lesions to cirrhosis. In practice, the adoption of this puncture assembly for portal vein branch puncture has a low hit rate, which not only causes more pain for the patient, but also requires the doctor and the patient to suffer a larger dose of X-ray irradiation. More seriously, this may also cause the surgery implementer to penetrate the liver capsule into the main portal vein of the liver by mistake, resulting in serious complications such as massive abdominal hemorrhage or the like.

Therefore, generally before performing intrahepatic portal vein branch puncture, the surgery implementer must carefully study the results of portal venography, and manually adjusts RUPS-100 by hands in vitro (in most cases, it is necessary to increase the bending angle of the puncture needle) based on position and shape of the portal vein and the relationship between the hepatic vein and the portal vein branch all of which are displayed by the above portal venography, and the anatomical relationship between hepatic and portal veins usually varies greatly from individual to individual. Whether the bending angle of the metal guide tube is appropriate and whether the inner diameter is curved to be flat can only depend on the experience of the surgery implementer.

Since the surgery is performed with the eye of the doctor, the position of the puncture needle and the position relationship between the puncture needle and various parts of the subject's body are judged during the surgery also depending on the experience of the surgery implementer.

In addition, because the subject's body position during the surgery and breathing movements may cause liver displacement and thus results in position deviation, even an experienced implementer usually needs to perform many times of puncture (about 5 to 8 times, even 10 to 15 times) to achieve success. The more the times of puncture is, the more opportunities the occurrence of complications is, and this is also the cause of postoperative restenosis and acute thrombosis (Li Yanhao. Diagram of Practical Clinical Interventional Diagnosis and Treatment [M]. Beijing: Science Press, 2012.).

Therefore, it has become an urgent problem to solve the monitoring blind zone, real-time monitoring and guiding the puncture instrument to the predetermined position of the portal vein via hepatic vein safely and effectively by the puncture navigation technology, and reducing complications. Therefore, there is an urgent need for a puncture instrument which can be applied to interventional navigation technology to operate a puncture surgery that is easier to operate, more accurate and effective, and safer under interventional navigation.

SUMMARY

Accordingly, embodiments of the present disclosure provide a puncture instrument to solve one or more of the above problems of the existing puncture surgery that has a high degree of operation difficulty, poor accuracy and poor safety, so as to operate a puncture surgery that is easier to operate, more accurate and effective, and safer.

According to one aspect of the disclosure, the disclosure provides a puncture instrument, including: a puncture needle which includes a sensor mounting portion capable of mounting an electromagnetic sensor.

Further, the sensor mounting portion is an internal cavity of the puncture needle or a concave portion of body surface of the puncture needle.

Further, the puncture needle is tubular, one end of a tubular cavity of the puncture needle is opened at a proximal end of the puncture needle, the other end of the tubular cavity is closed at a distal end of the puncture needle, and the tubular cavity forms the sensor mounting portion.

Further, the puncture needle includes a needle head and a needle rod, and the needle head and the needle rod are formed integrally.

Further, the puncture needle includes a needle head and a needle rod, and the needle head and the needle rod are connected by welding or threading.

Further, the proximal end of the needle head includes a connection portion, the needle rod is tubular, and when the needle head is connected with the needle rod, the connection portion is inserted into the tubular cavity of the needle rod.

Further, an outer diameter of a distal portion of the needle rod is smaller than an outer diameter of a proximal portion of the needle rod.

Further, the needle rod includes an inner needle rod and an outer needle rod, and the outer needle rod sleeves outside the inner needle rod, and the outer needle rod is connected with the inner needle rod by welding.

Further, the inner needle rod and the outer needle rod are sealed by welding or bonding.

Further, at the distal portion of the needle rod, the inner needle rod extends beyond the outer needle rod.

Further, the puncture needle includes an auxiliary portion, the auxiliary portion sleeves outside the needle rod, and a friction coefficient of the auxiliary portion is smaller than that of the needle rod.

Further, the auxiliary portion is a spring or a sleeve.

Further, the spring is connected with the needle rod by welding.

Further, a material of the sleeve is polytetrafluoroethylene, and the sleeve is connected with the needle rod by means of heat shrinkage.

Further, the outer diameter of a distal portion of the needle rod is smaller than an outer diameter of a proximal portion of the needle rod, and the spring or the sleeve sleeves at the distal portion of the needle rod.

Further, the outer needle rod includes a distal outer needle rod and a proximal outer needle rod, the distal outer needle rod sleeves at a distal end of the inner needle rod, the proximal outer needle rod sleeves at a proximal end of the inner needle rod, and the spring or the sleeve sleeves outside the inner needle rod between the distal outer needle rod and the proximal outer needle rod.

Further, an outer diameter of a distal portion of the inner needle rod is smaller than an outer diameter of a proximal portion of the inner needle rod, and the outer needle rod and the spring sequentially sleeve at the distal portion of the inner needle rod from the distal end to the proximal end, or the outer needle rod and the sleeve sequentially sleeve at the distal portion of the inner needle rod from the distal end to the proximal end.

Further, at the distal portion of the needle rod, the inner needle rod extends beyond the outer needle rod, and the spring or the sleeve sleeves at the portion of the inner needle rod that extends beyond the outer needle rod.

Further, the electromagnetic sensor is a wireless sensor or a wired sensor.

Further, a material of the puncture needle includes but is not limited to one or more selected from stainless steel, and nickel-titanium alloy.

Further, a thickness specification of the puncture needle includes but are not limited to: 16 G, 17 G, 18 G, 19 G, 20 G, and 21 G.

Further, a material of the spring includes but is not limited to one or more selected from stainless steel, nickel-titanium alloy, cobalt-based alloy, and titanium-based alloy.

Further, the puncture instrument includes an interventional catheter instrument, which includes: a guide tube; and a flexible sleeve which sleeves outside the guide tube; and the flexible sleeve and the guide tube are capable of moving relatively to each other so that a distal end of the flexible sleeve extends beyond a distal end of the guide tube, or the distal end of the guide tube extends beyond the distal end of the flexible sleeve.

Further, the distal end of the flexible sleeve is provided with a shrunk portion, an inner diameter of the shrunk portion is smaller than the outer diameter of the guide tube, and the shrunk portion is provided with a weakened portion which is easy to be damaged; when the interventional catheter instrument abuts against a puncture target, the weakened portion is capable of being destroyed by causing the guide tube to move to the distal end relative to the flexible sleeve, so that the guide tube extends beyond the distal end of the flexible sleeve.

Further, the weakened portion extends to a distal opening of the flexible sleeve.

Further, the weakened portion extends to the distal opening of the flexible sleeve in a longitudinal direction of the flexible sleeve in a straight or helical manner.

Further, the weakened portion is an intermittent indent line or indentation.

Further, the weakened portion is provided on an inner surface or an outer surface of the shrunk portion.

Further, the inner diameter of the shrunk portion is smaller than the outer diameter of the guide tube of 0.05 mm to 1 mm.

Further, a material of the flexible sleeve includes, but are not limited to, one or more selected from polytetrafluoroethylene, fluorinated ethylene propylene copolymer, thermoplastic polyurethane elastomer, nylon 12, block polyether amide elastomer, high density poly-ethylene.

Further, a material of the guide tube includes but is not limited to one or more selected from stainless steel, and nickel-titanium alloy.

Further, a thickness specification of the guide tube includes but are not limited to: 13 G, 14 G, 15 G, and 16 G, and a length of the guide tube is 42 cm to 57 cm.

Further, the inner diameter of the flexible sleeve is greater than the outer diameter of the guide tube of 0.1 mm to 2 mm.

Further, the interventional catheter instrument includes a connector through which a proximal end of the guide tube is connected with a proximal end of the flexible sleeve, and the guide tube and the flexible sleeve are able to move relative to each other through the connector.

Further, a connection method of the connector includes threaded connection, clasping connection or bonding connection.

In conclusion, the puncture instrument according to the present disclosure can implement a puncture surgery that is easier to operate, more accurate and effective, safer under the interventional navigation technology, thus solving the technical problems existing in the prior art.

BRIEF DESCRIPTION OF THE DRAWINGS

The features and advantages of the disclosure will become more easily understood by the following specific embodiments provided with reference to the attached drawings, in the drawings.

DESCRIPTION OF THE EMBODIMENTS

Figure 1:
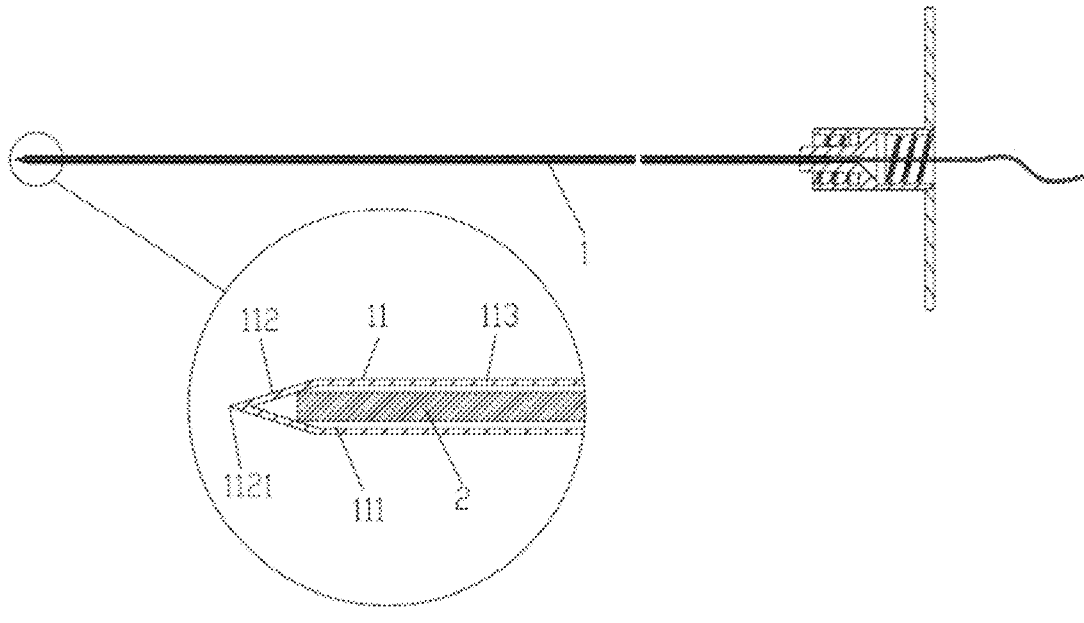
FIG. 1 is a schematic diagram of a puncture instrument according to an embodiment of the present disclosure.

The exemplary embodiments of the present disclosure are described below in detail with reference to the attached drawings. The description of the exemplary embodiments is for illustration purposes only and is in no way a limitation to the present disclosure, its application or usage.

In order to make the purpose, advantages and features of the disclosure clearer, the disclosure is further illustrated in detail in combination with the attached drawings. It should be noted that the drawings are in a very simplified form and use imprecise proportions only to conveniently and clearly assist in stating the purpose of embodiments of the disclosure.

As used in the present disclosure, the singular forms “a”, “an”, and “the” include plural objects, unless the content expressly states otherwise. As used in the present disclosure, the term “or” is generally used in a sense that includes “and/or” unless otherwise expressly stated in the content. The “distal end” and “distal side” mentioned in the present disclosure refer to the side far away from the operator; and accordingly, “proximal end” and “proximal side” refer to the side opposite to “distal end” and “distal side”.

In order to solve problems of the puncture surgery that has a high degree of operation difficulty, poor accuracy and poor safety and the like, to implement a puncture surgery that is easier to operate, more accurate and effective, safer, the interventional navigation technology can be utilized, such as an electromagnetic navigation technology.

The electromagnetic navigation device uses electromagnetic induction to measure the position and direction of an object based on the Biot-Savart law, in which a magnetic field signal sender generates a signal field by sending a magnetic field signal, and a magnetic signal receiving sensor receives the magnetic field signal and transmits the magnetic field signal to a magnetic field signal controller to obtain space vector information (space coordinates and direction) of the object.

At present, the more widely used electromagnetic navigation products are POLARIS system of Canada NDI company, VISLAN system of British RMR company, STEALTHSTATION system of American MEDTRONIC company, etc. The POLARIS system has a measurement accuracy of 0.35 mm. The RMS is considered as the international standard for the navigation positioning system and is capable of simultaneously tracking nine passive surgical instruments and three active surgical instruments.

The sender of the electromagnetic navigation device usually includes an electromagnetic sender coil to emit electromagnetic waves and generate an electromagnetic field. The effective positioning range of the electromagnetic field may be 300 mm×300 mm×300 mm, and 400 mm×400 mm×400 mm, etc.

The sensor of the electromagnetic navigation device can receive an electromagnetic signal through an electromagnetic receiving coil, and convert the electromagnetic signal into an electrical signal to track and position the position of the sensor in the electromagnetic field.

According to clinical requirements, the positioning accuracy of navigation is usually up to 5 mm and the positioning speed is up to 30 ms. In the embodiment of the present disclosure, the minimum accuracy of electromagnetic positioning can be 1.5 mm, and the maximum positioning speed can be 12.5 ms.

According to the application needs, the sensor may be designed into various structures and sizes, and the sensor in the embodiment of the present disclosure may be linear, and its size may be the minimum outer diameter of 0.56 mm, as shown in FIG. 1.

The sensor may be wired or wireless, thus the connection between the electromagnetic device and the puncture instrument may be wired or wireless, and for example, the wireless connection can be Bluetooth, WIFI, Zigbee, etc.

The embodiment of the present disclosure provides a puncture instrument which can be applied to interventional navigation technology, the puncture instrument may be provided with an above sensor through which, in combination with an ultrasonic imaging device, the puncture instrument can be positioned and navigated during the puncture surgery.

FIG. 1 is a schematic diagram of a puncture instrument according to an embodiment of the present disclosure. As shown in FIG. 1, in the embodiment of the disclosure, the puncture instrument 1 may include a puncture needle 11, which may be provided with a sensor mounting portion 111, and the sensor mounting portion 111 may be configured to mount a sensor 2.

In the embodiment of the disclosure, a material of the puncture needle 11 may include, but is not limited to, one or more selected from stainless steel, and nickel-titanium alloy.

According to the requirements of clinical application, a thickness specification of the puncture needle 11 may include, but is not limited to: 16 G, 17 G, 18 G, 19 G, 20 G, and 21 G, etc. (G is the abbreviation of GAUGE, a length metering unit of diameter originating in North America).

According to the requirements of clinical application, the puncture needle 11 may be designed in various lengths, for example, for transjugular intrahepatic portosystemic shunt, the length specification may be 50 cm to 65 cm.

Figure 3:
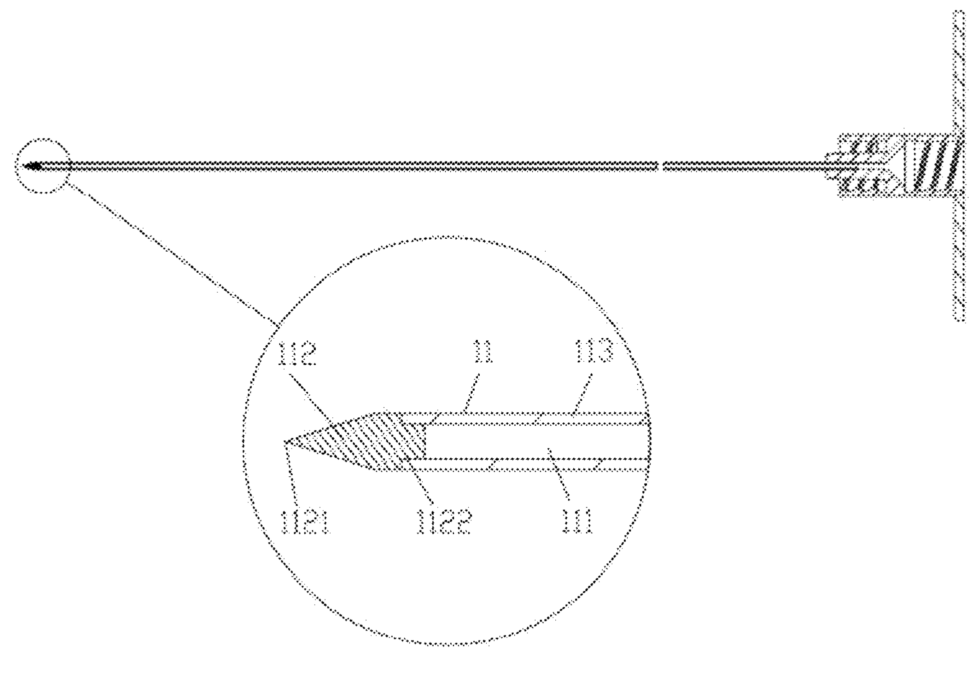
FIG. 3 is a schematic diagram of a puncture needle according to an embodiment of the present disclosure.

As shown in FIG. 1, the puncture needle 11 may include a needle head 112 and a needle rod 113. In the embodiment of the disclosure, the needle head 112 and the needle rod 113 may be formed integrally, as shown in FIG. 1. The needle head 112 and the needle rod 113 may also be assembly connected separately. For example, the needle head 112 and the needle rod 113 are connected by welding, threading, etc., as shown in FIG. 3.

In the embodiment of the present disclosure, a needle tip 1121 of the needle head 112 may be of a triangular pyramid, a rectangular pyramid or conical. The height of the taper of the needle tip 1121 may be 1 mm to 4 mm.

Since the puncture surgery navigation usually requires positioning the distal end of the puncture needle, in the embodiment of the present disclosure, the sensor mounting portion 111 may be provided on the distal end of the puncture needle 11.

In the embodiment of the present disclosure, the sensor mounting portion 111 may be an internal cavity of the puncture needle 11, as shown in FIG. 1. If the sensor is wired, the cavity may be provided with an opening for the pass-through of the wire. For example, the cavity is opened at the proximal end of the puncture needle 11. If the sensor is wireless, the cavity may be closed after the sensor is installed.

In the embodiment of the present disclosure, the distance between the cavity of the puncture needle 11 and the needle tip of the puncture needle 11 may be 0.10 mm to 30 mm.

As shown in FIG. 1, the puncture needle 11 may be tubular, one end of a tubular cavity of the puncture needle 11 is opened at a proximal end of the puncture needle 11, the other end of the tubular cavity is closed at a distal end of the puncture needle, and the sensor mounting portion 111 is formed by the tubular cavity.

Figure 2:
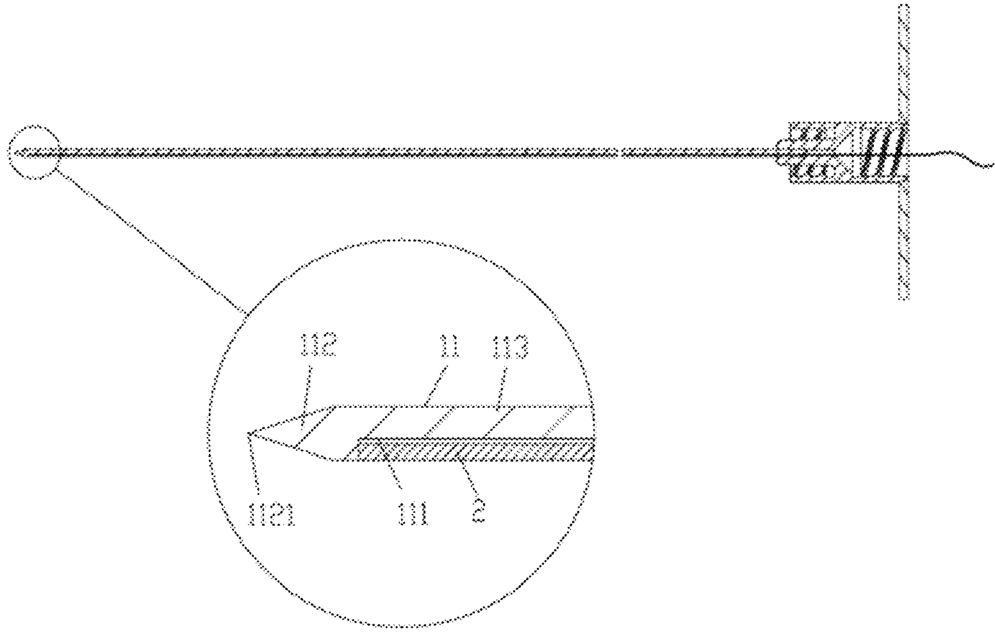
FIG. 2 is a schematic diagram of a puncture instrument according to an embodiment of the present disclosure.

FIG. 2 is a schematic diagram of a puncture instrument according to an embodiment of the present disclosure. As shown in FIG. 2, in the embodiment of the present disclosure, the sensor mounting portion 111 may be a concave portion of body surface of the puncture needle 11.

FIG. 3 is a schematic diagram of a puncture needle according to an embodiment of the present disclosure. As shown in FIG. 3, the proximal end of the needle head 112 may include a connection portion 1122, and an outer diameter of the connection portion 1122 is smaller than an inner diameter of the tubular cavity of the needle rod 113. When the needle head 112 is connected to the needle rod 113, the connection portion 1122 is capable of being inserted into the tubular cavity of the needle rod 113.

In order to adapt to a tortuous and narrow puncture path and increase the flexibility and guidance of the puncture needle 11, in the embodiment of the present disclosure, the needle rod 113 may be set as a variable-diameter shape, and the outer diameter of the distal portion of the needle rod 113 is smaller than the outer diameter of the proximal portion of the needle rod 113. A transition between the two outer diameter portions may be gradual or stepped.

Figure 4:
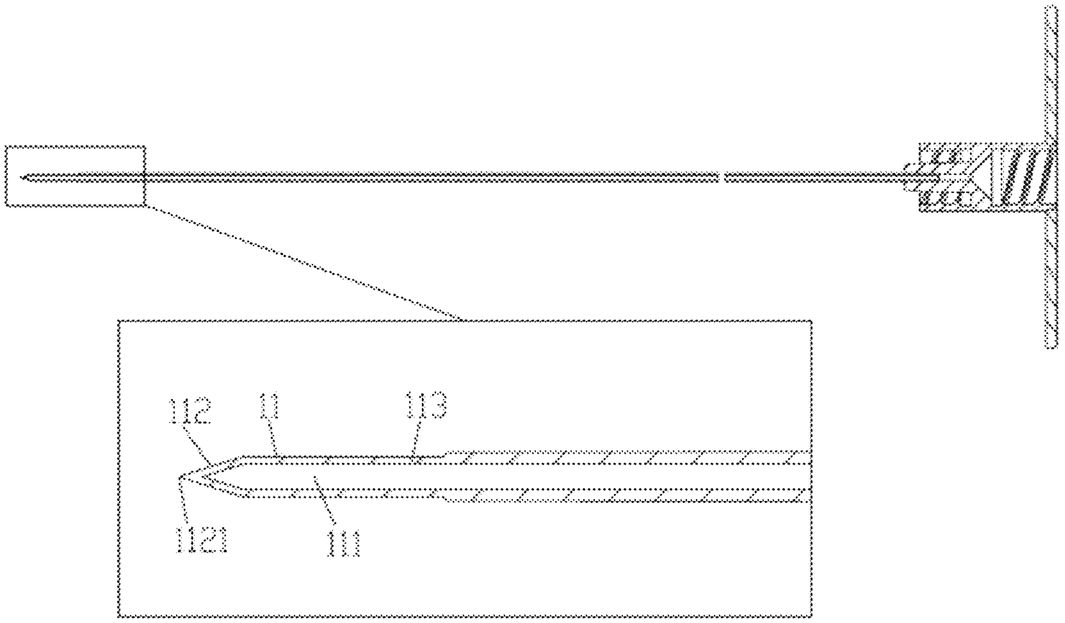
FIG. 4 is a schematic diagram of a puncture needle according to an embodiment of the present disclosure.

FIG. 4 is a schematic diagram of a puncture needle according to an embodiment of the present disclosure. As shown in FIG. 4, the outer diameter of the distal portion of the needle rod 113 is smaller than the outer diameter of the proximal portion of the needle rod 113, and a transition between the two outer diameter portions may be stepped. The flexibility and guidance of the needle rod 113 may be effectively increased by above reduced variable-diameter shape.

In order to adapt to a tortuous puncture path and increase the flexibility and guidance of the puncture needle 11, in the embodiment of the present disclosure, the needle rod may also be configured to include an inner needle rod and an outer needle rod.

Figure 5:
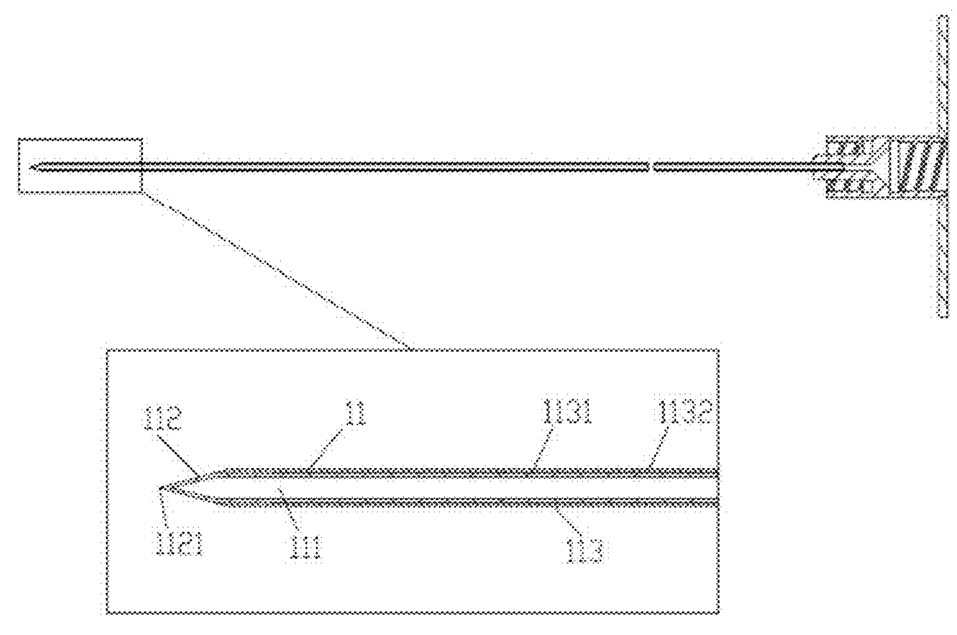
FIG. 5 is a schematic diagram of a puncture needle according to an embodiment of the present disclosure.

FIG. 5 is a schematic diagram of a puncture needle according to an embodiment of the present disclosure. As shown in FIG. 5, the needle rod 113 may include an inner needle rod 1131 and an outer needle rod 1132, and the outer needle rod 1132 sleeves outside the inner needle rod 1131. The outer needle rod 1132 and the inner needle rod 1131 may be connected by welding, threading, etc. In addition, in order to prevent body fluids from entering between the inner needle rod 1131 and the outer needle rod 1132, sealing treatment is required between the inner needle rod 1131 and the outer needle rod 1132, and the sealing treatment may be achieved by welding or bonding.

Figure 6:
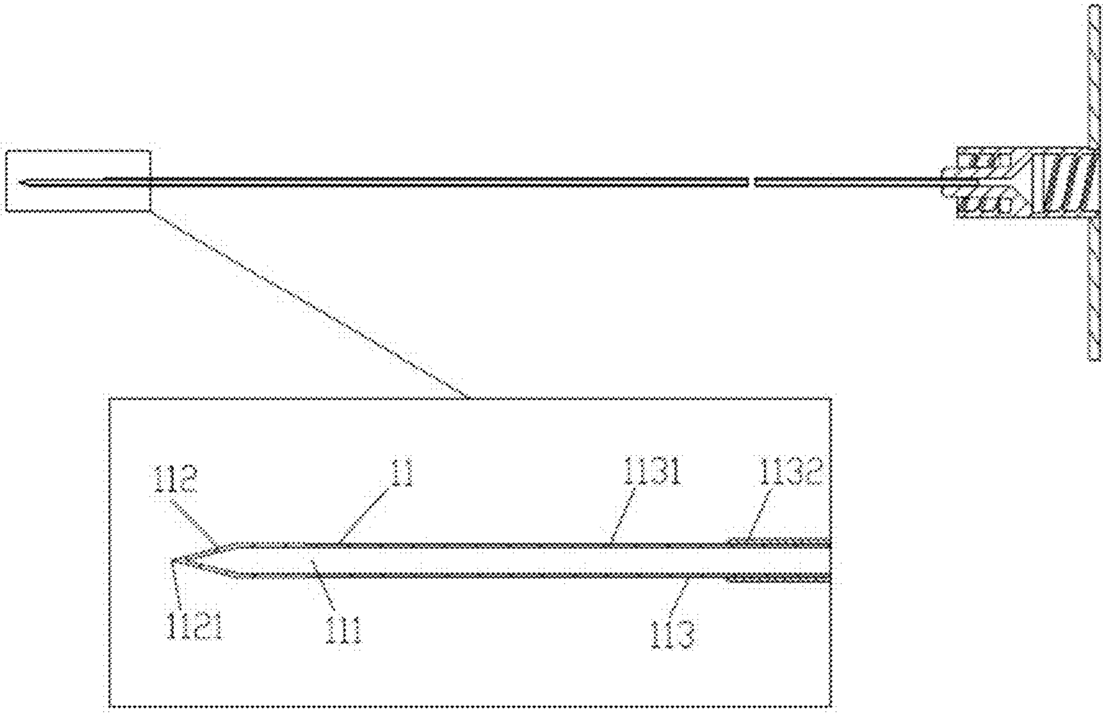
FIG. 6 is a schematic diagram of a puncture needle according to an embodiment of the present disclosure.

In the embodiment of the present disclosure, the design of the reduced variable-diameter needle rod may be combined with the design of the inner needle rod and the outer needle rod. FIG. 6 is a schematic diagram of a puncture needle according to an embodiment of the present disclosure. As shown in FIG. 6, at the distal portion of the needle rod 113, the inner needle rod 1131 extends beyond the outer needle rod 1132, resulting in a reduced variable-diameter needle rod design.

In order to adapt to a tortuous and narrow puncture path, effectively reduce the friction resistance of the puncture needle 11 and improve the operation stability of the puncture needle 11, in the embodiment of the present disclosure, the puncture needle may also be configured to include an auxiliary portion, and the auxiliary portion may be a spring or a sleeve.

The spring can effectively reduce the contact area between the outer surface of the puncture needle 11 and the surrounding material, thereby reducing its friction resistance. In addition, due to its elastic tensile force and the effect of increasing the radial size of the puncture needle 11, the spring can improve the operation stability of the puncture needle 11.

The spring can sleeve on the needle rod and can be connected to the needle rod by welding. For example, both ends of the spring may be welded separately to the needle rod.

The sleeve can be made of a material with a low friction coefficient to reduce friction resistance, such as polytetrafluoroethylene (PTFE) material. The friction coefficient of polytetrafluoroethylene (PTFE) is very low, and the friction coefficient of polytetrafluoroethylene on steel is often quoted as 0.04. In addition, due to its elastic tensile force and the effect of increasing the radial size of the puncture needle 11, the sleeve can improve the operation stability of the puncture needle 11.

In the embodiment of the present disclosure, the sleeve can sleeve on the needle rod by means of heat shrinkage.

Figure 7:
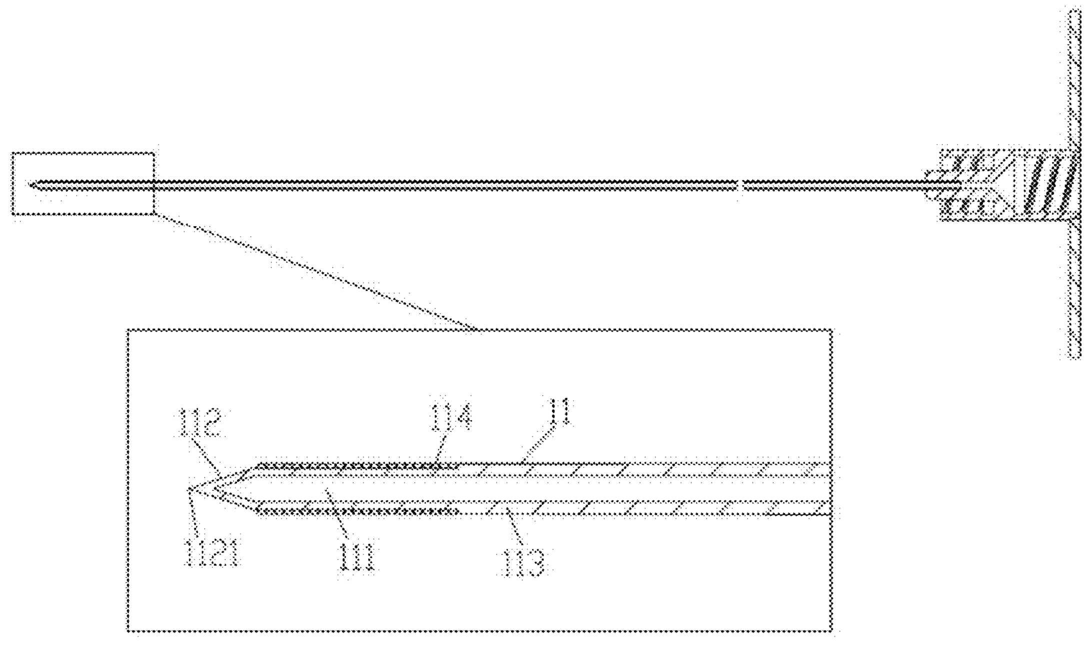
FIG. 7 is a schematic diagram of a puncture needle provided with a spring according to an embodiment of the present disclosure.

FIG. 7 is a schematic diagram of a puncture needle provided with a spring according to an embodiment of the present disclosure. As shown in FIG. 7, the needle rod 113 may be a variable-diameter shape, and the outer diameter of the distal portion of the needle rod 113 is smaller than the outer diameter of the proximal portion of the needle rod 113, and the spring 114 sleeves at the distal portion with a smaller outer diameter of the needle rod 113. The spring 114 may be connected with the needle rod 113 by welding.

In the embodiment of the present disclosure, a material of the spring 114 may include, but is not limited to one or more selected from stainless steel, nickel-titanium alloy, cobalt-based alloy, and titanium-based alloy.

In the embodiment of the disclosure, a dimension of the spring 114 may be: diameter of a spring wire of 0.08 mm to 0.3 mm, mean diameter of coil of 0.5 mm to 2.0 mm, free length of the spring of 30 mm to 200 mm.

Figure 8:
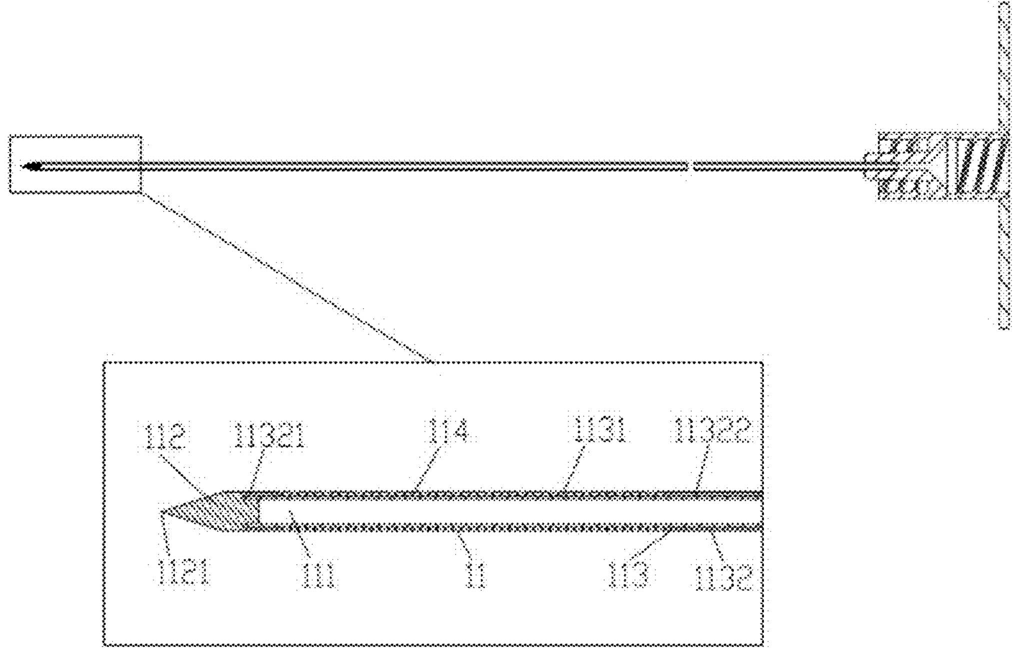
FIG. 8 is a schematic diagram of a puncture needle provided with a spring according to an embodiment of the present disclosure.

FIG. 8 is a schematic diagram of a puncture needle provided with a spring according to an embodiment of the present disclosure. As shown in FIG. 8, in the embodiment of the present disclosure, the outer needle rod 1132 may include a distal outer needle rod 11321 and a proximal outer needle rod 11322. The distal outer needle rod 11321 sleeves on a distal end of the inner needle rod 1131, the proximal outer needle rod 11322 sleeves on a proximal end of the inner needle rod 1131, and the spring 114 may be provided between the distal outer needle rod 11321 and the proximal outer needle rod 11322, and sleeves on the inner needle rod 1131.

Figure 9:
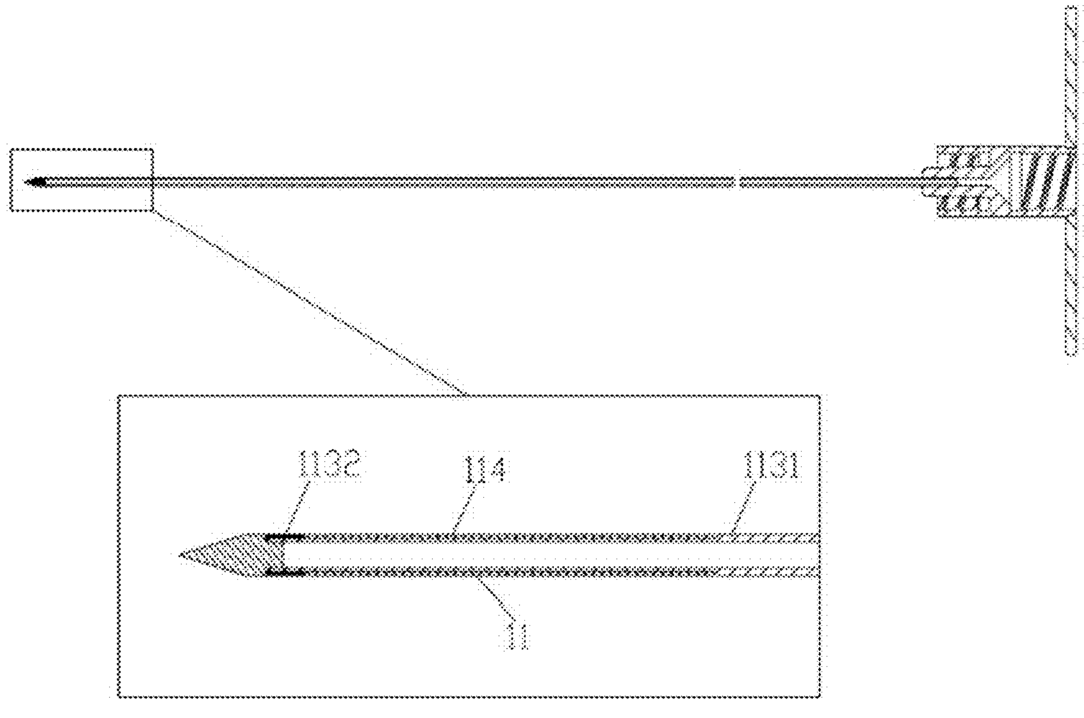
FIG. 9 is a schematic diagram of a puncture needle provided with a spring according to an embodiment of the present disclosure.

FIG. 9 is a schematic diagram of a puncture needle provided with a spring according to an embodiment of the present disclosure. As shown in FIG. 9, in the embodiment of the present disclosure, the inner needle rod 1131 may be a variable-diameter shape, and an outer diameter of a distal portion of the inner needle rod 1131 is smaller than an outer diameter of a proximal portion of the inner needle rod 1131. As shown in FIG. 9, the outer needle rod 1132 and the spring

114 sequentially sleeve at the distal portion of the inner needle rod 1131 from the distal end to the proximal end.

In the embodiment of the present disclosure, the spring may also sleeve on a portion of the inner needle rod 1131 that extends beyond the outer needle rod 1132 in the embodiment of the disclosure as shown in FIG. 6.

The assembly relationship between the sleeve and the needle rod may be the same as the assembly relationship between the spring and the needle rod, as described above.

Figure 10:
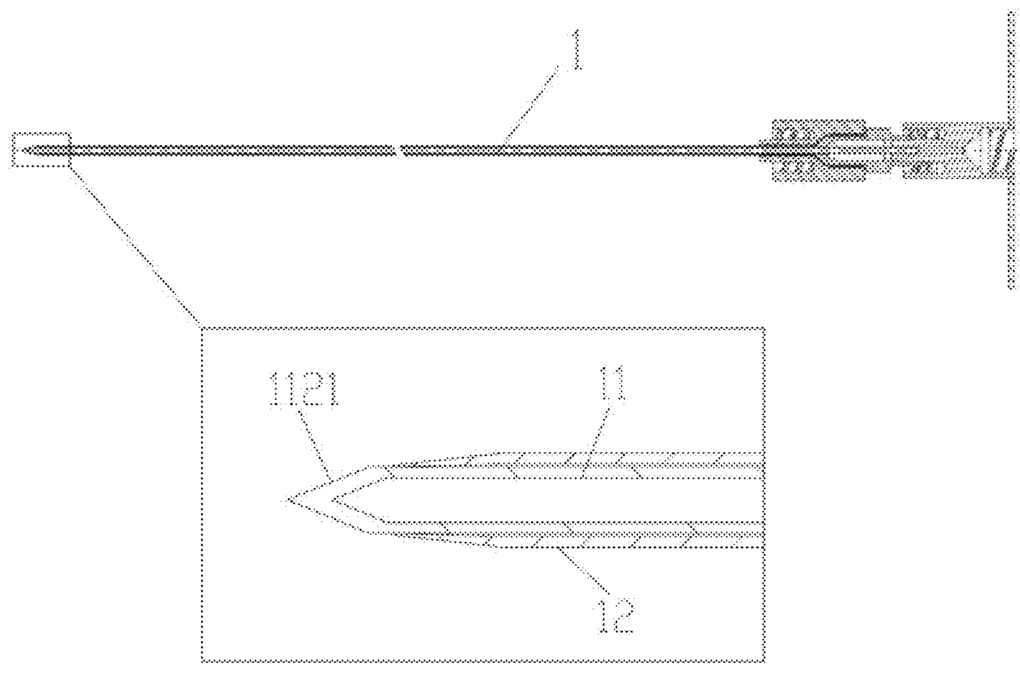
FIG. 10 is a schematic diagram of a puncture needle provided with a catheter according to an embodiment of the present disclosure.

FIG. 10 is a schematic diagram of a puncture needle provided with a catheter according to an embodiment of the present disclosure. As shown in FIG. 10, in the embodiment of the present disclosure, the puncture instrument 1 may include a catheter 12. On one hand, the catheter 12 can be used to establish a channel to transport the guide wire; on the other hand, the catheter 12 can protect the outer surface of the puncture needle 11 to prevent the formation of thrombus and reduce the friction resistance of the puncture needle 11 during movement.

As shown in FIG. 10, the catheter 12 may sleeve outside the puncture needle 11. The distal end of the catheter 12 may be processed by tip molding. After assembly, the distal end of the catheter 12 is located on a proximal side of the conical bottom face of the needle tip 1121 of the puncture needle 11, and the distance between the distal end of the catheter 12 and the conical bottom surface of the needle tip 1121 may be 0 mm to 1 mm, forming interference or transitional fit, exemplarily transitional fit. The proximal end of the catheter 12 may be threaded to the proximal end of the puncture needle 11 by a connector.

Catheterization is widely used in interventional radiology. Most of the catheter instruments used in the past were used to establish the channel for interventional surgical instruments, and most of them did not have the function of specific position bending guidance (Li Yanhao. Diagram of Practical Clinical Interventional Diagnosis and Treatment [M]. Beijing: Science Press, 2012.).

At present, some of the catheter instruments used clinically in human blood vessels and organs need to be bent at a certain angle at a specific position after entering the human body, and guide the interventional surgical instruments such as a puncture needle and a guide wire after bending. For example, the plastic catheter instrument and metal catheter instrument of the RUPS-100 puncture assembly produced by COOK in the United States have a bending and guiding structure at a specific position to achieve the corresponding guiding function.

In the process of intervention, sometimes in order to achieve the guidance of intervention, the distal end of the catheter instrument is required to abut against the interventional target, so that the interventional instrument passes through the catheter instrument and extends beyond the distal end of the catheter instrument, and accurately intervenes at the interventional target.

In order to prevent the distal end of the catheter instrument from causing injury to the tissue when it passed by in the process of passing through the intervention pathway to reach the interventional target, a flexible sleeve may be provided outside the catheter, the flexible sleeve extends beyond the distal end of the catheter, so that the distal end of the catheter is covered by the flexible sleeve to prevent it from harming the surrounding tissues.

In the interventional surgery, especially the interventional surgery with a long and tortuous intervention pathway, the interventional instrument is required to bend at a certain angle in the blood vessel through the catheter instrument before conducting blood vessel or tissue intervention. When the distal end of the flexible sleeve sleeving outside the catheter abuts against the interventional target, due to the flexibility of the flexible sleeve, the flexible sleeve cannot be kept at the interventional target during the intervention process, which often leads to errors such as failure in threading a needle or the change of the intervention direction during the intervention process, resulting in very difficult operation for the surgery implementer. At present, it can only rely on surgical practitioners to extracorporeal catheter support or pressure on specific parts of the human body, which greatly increases the difficulty of operation of the practitioners and limits the application of surgery.

For example, in transjugular intrahepatic puncture surgery, keeping the catheter instrument at the puncture target on the wall of the hepatic vein is the key to the success of the surgical puncture (Li Yanhao. Diagram of Practical Clinical Interventional Diagnosis and Treatment [M]. Beijing: Science Press, 2012.). However, the current puncture assembly cannot effectively solve this problem (Chu Jianguo, Development status and standardization of transjugular intrahepatic portal shunt technique in China, Chin Journal Interventional Radiology (Electronic Edition), 2013, 1 (2)).

Therefore, there is an urgent need for a catheter instrument that can not only prevent damage to the surrounding tissues the catheter instrument passes, but also be kept at the interventional target during the intervention process, so as to prevent errors such as puncture failure in threading a needle or the change of the intervention direction during the intervention process.

Figure 11:
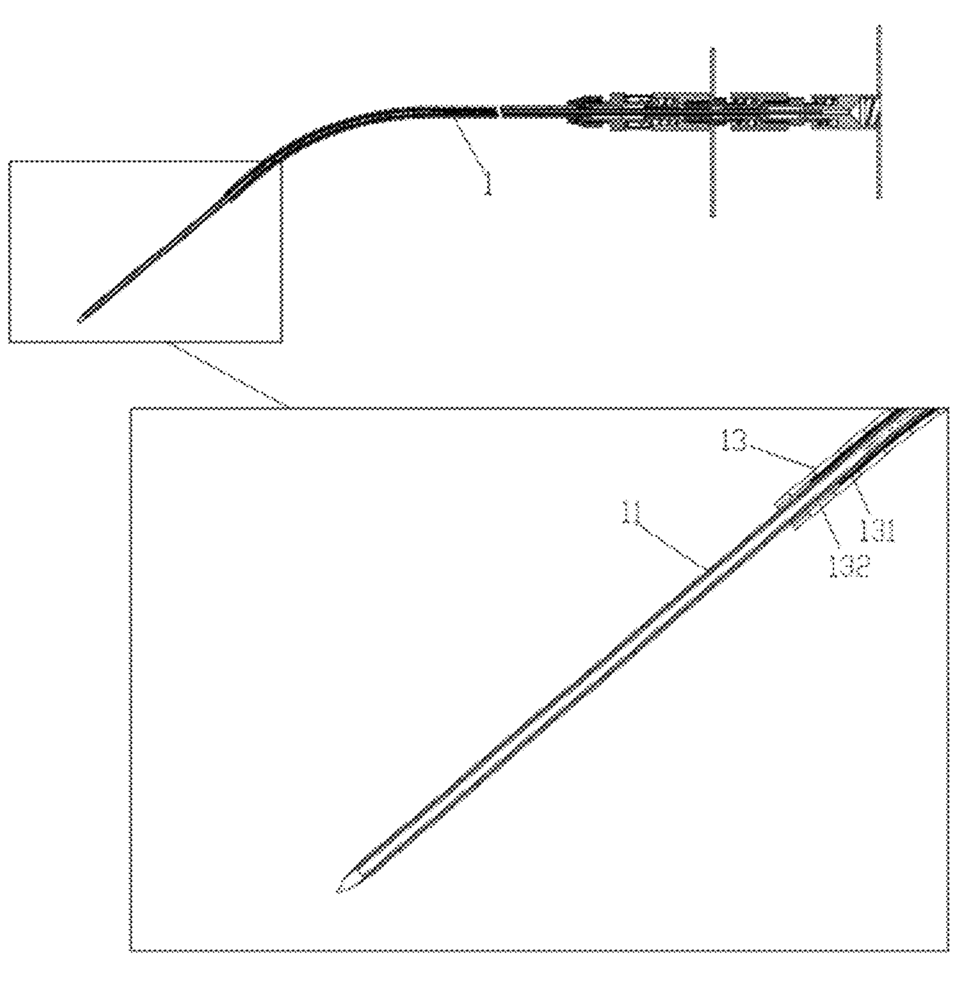
FIG. 11 is a schematic diagram of assembling an interventional catheter instrument and a puncture needle according to an embodiment of the present disclosure.

In the embodiment of the present disclosure, the puncture instrument 1 may include a catheter instrument 13. FIG. 11 is a schematic diagram of assembling an interventional catheter instrument and a puncture needle according to an embodiment of the present disclosure. In the embodiment of the present disclosure, as shown in FIG. 11, the catheter instrument 13 may include a guide tube 131 and a flexible sleeve 132, to provide guidance for a puncture needle 11. Depending on clinical needs, the catheter instrument 13 may be linear or curved, and for example, the curved ones may be used in the transjugular intrahepatic puncture surgery.

Figure 12:
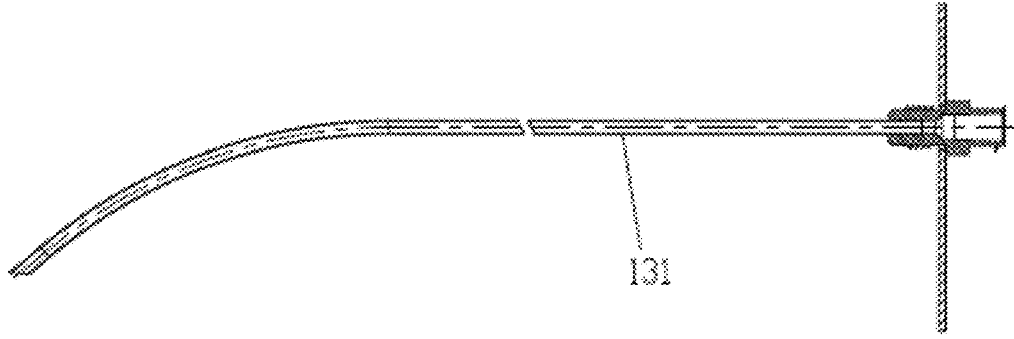
FIG. 12 is a schematic diagram of a guide tube according to an embodiment of the present disclosure.

FIG. 12 is a schematic diagram of a guide tube according to an embodiment of the present disclosure. In the embodiment of the present disclosure, a material of the guide tube 131 may include, but is not limited to, one or more selected from stainless steel, and nickel-titanium alloy. Depending on clinical needs, a thickness specification of the guide tube 131 may include, but is not limited to: 13 G, 14 G, 15 G, 16 G, etc. (G is the abbreviation of GAUGE, a length metering unit of diameter originating in North America); and a length specification may be 42 cm to 57 cm.

As shown in FIG. 12, the distal end of the guide tube 131 may be of an oblique blade type, which can be used for puncture or for penetrating into the interventional target so as to abut against the interventional target.

As shown in FIG. 12, the distal side of the guide tube 131 may be curved at one or more places according to clinical needs. In an embodiment of the present disclosure, the distal end of the guide tube 131 is of a curved oblique blade type, which may be bent at 10° to 80° at a distance of 0.5 cm to 12 cm from the tip of the oblique blade, for example, may be bent at 60°.

Figure 13:
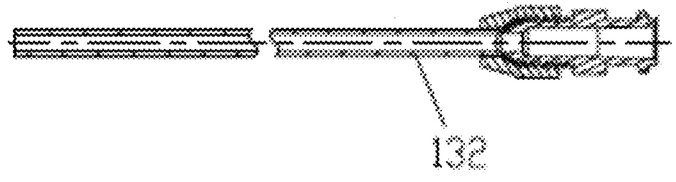
FIG. 13 is a schematic diagram of a flexible sleeve according to an embodiment of the present disclosure.

FIG. 13 is a schematic diagram of a flexible sleeve according to an embodiment of the present disclosure. In the embodiment of the present disclosure, a material of the flexible sleeve 132 may include, but are not limited to, one or more selected from polytetrafluoroethylene (PTFE), fluorinated ethylene propylene copolymer (FEP), thermoplastic polyurethane elastomer (TPU), Polyamide 12 (PA12), Polyether Block Amide (Pebax), high density polye-thylene (HDPE) and the like.

Figure 14:
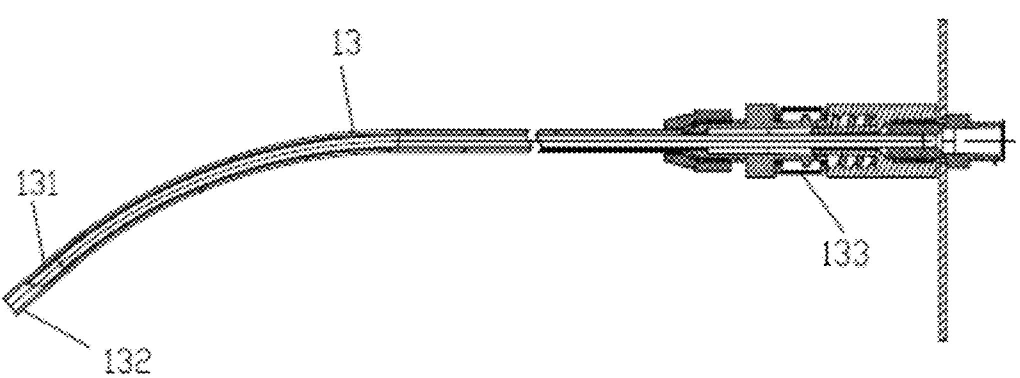
FIG. 14 is a schematic diagram of assembling a guide tube and a flexible sleeve according to an embodiment of the present disclosure.

FIG. 14 is a schematic diagram of assembling a guide tube and a flexible sleeve according to an embodiment of the present disclosure. In the embodiment of the present disclosure, as shown in FIG. 14, the flexible sleeve 132 may sleeve outside the guide tube 131, and its inner diameter is larger than the outer diameter of the guide tube 131 of 0.1 mm to 2 mm. The guide tube 131 and the flexible sleeve 132 may be moved relative to each other so that the distal end of the guide tube 131 may extend beyond the distal end of the flexible sleeve 132, or the distal end of the flexible sleeve 132 may extend beyond the distal end of the guide tube 131 (as shown in FIG. 14).

In the embodiment of the present disclosure, the proximal end of the flexible sleeve 132 may be connected with the proximal end of the guide tube 131 by threading, clasping or bonding through the connector 133, and the flexible sleeve 132 and the guide tube 132 can be moved relatively by the connector 133. As shown in FIG. 11 or 14, the proximal ends of the flexible sleeve 132 and the proximal end of the guide tube 131 are connected by threading through the connector 133.

Figure 15:
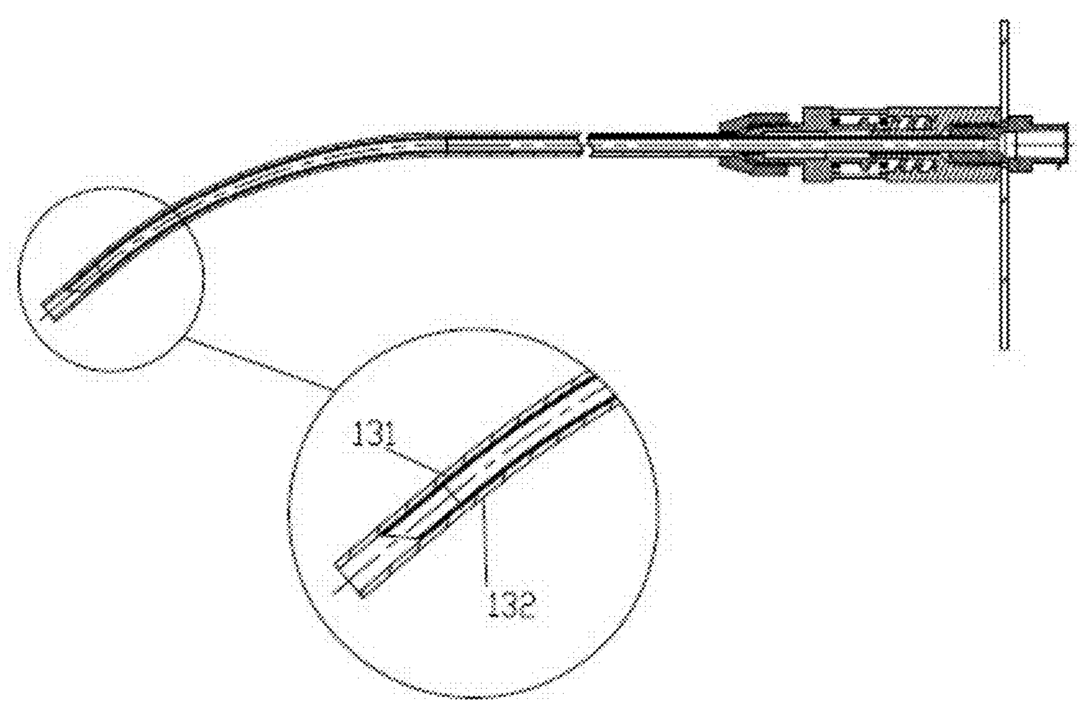
FIG. 15 is a state schematic diagram of the guide tube and flexible sleeve in the process of reaching a puncture target through an intervention pathway according to an embodiment of the present disclosure.

In the puncture surgery according to the embodiment of the present disclosure, the catheter instrument 13 including the guide tube 131 and the flexible sleeve 132 first enters the body via the intervention pathway through the skin or the organ cavity canals or the like to reach the puncture target. FIG. 15 is a state schematic diagram of the guide tube and flexible sleeve in the process of reaching a puncture target through an intervention pathway according to an embodiment of the present disclosure. As shown in FIG. 15, in this process, the flexible sleeve 132 sleeves outside the guide tube 131, and the distal end of the flexible sleeve 132 extends 2 mm to 3 mm beyond the distal oblique blade of the guide tube 131 to prevent the distal oblique blade from harming the tissue passed by.

Figure 16:
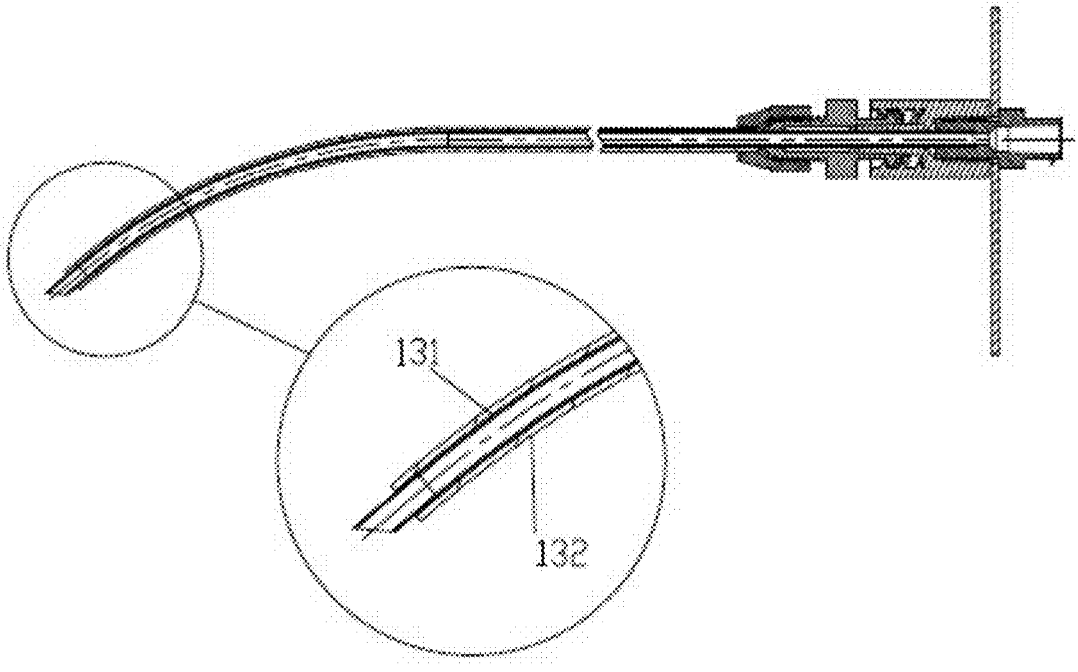
FIG. 16 is a state schematic diagram of the guide tube and the flexible sleeve when implementing puncture guidance according to an embodiment of the present disclosure.

In the puncture surgery according to the embodiment of the disclosure, when the distal end of the catheter instrument 1 reaches the puncture target, the guide tube 131 and the flexible sleeve 132 can be moved relative to each other, so that the distal end of the guide tube 131 extends beyond the distal end of the flexible sleeve 132, then the distal end of the guide tube 131 can be kept abutting against the puncture target to perform puncture guidance. FIG. 16 is a state schematic diagram of the guide tube and the flexible sleeve when implementing puncture guidance according to an embodiment of the present disclosure.

Figures 17, 18:
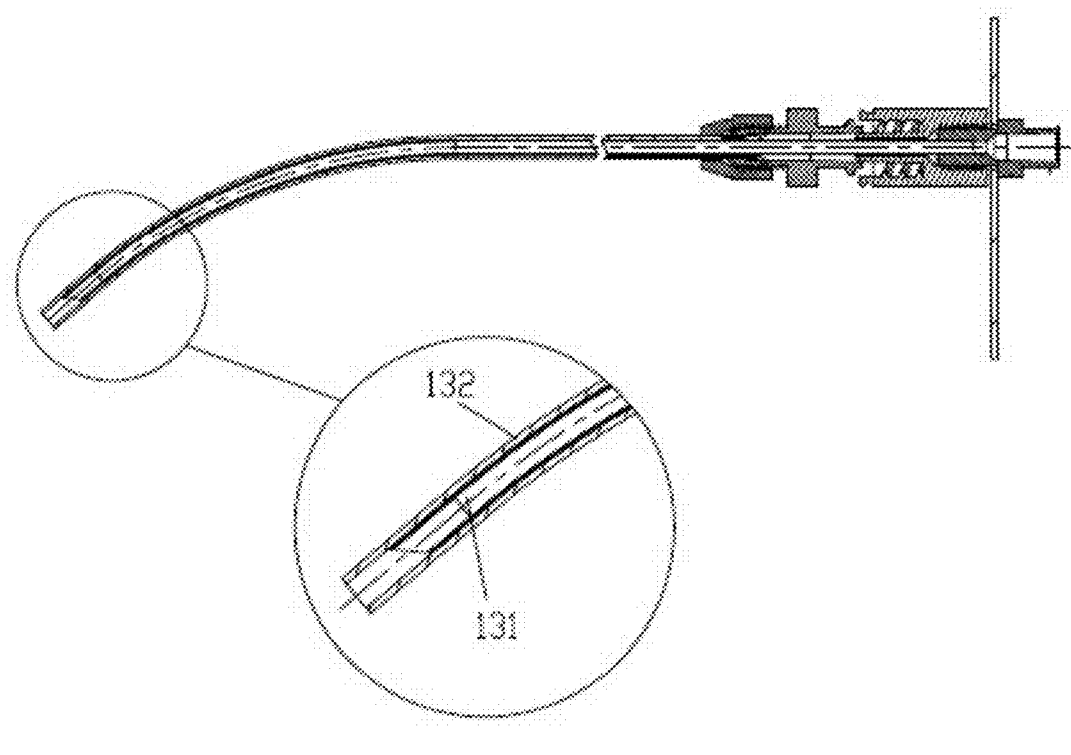
FIG. 17 is a state schematic diagram of the guide tube and flexible sleeve in the exiting process through the intervention pathway after puncture guidance according to an embodiment of the present disclosure.
FIG. 18 is a schematic diagram of a flexible sleeve formed by shrinking a distal end according to an embodiment of the present disclosure.

In the puncture surgery according to the embodiment of the disclosure, when the catheter instrument 13 is to exit through the intervention pathway after puncture guidance, the guide tube 131 and the flexible sleeve 132 can be moved relative to each other so that the distal end of the flexible sleeve 132 extends beyond the distal oblique blade of the guide tube 131 to prevent the distal oblique blade from harming the tissues passed by. FIG. 17 is a state schematic diagram of the guide tube and flexible sleeve in the exiting process through the intervention pathway after puncture guidance according to an embodiment of the present disclosure.

In the interventional diagnosis and treatment, the distal end of the catheter instrument is subjected to resistance from the tissues and organs it passes by in the process of reaching the interventional target through the intervention pathway, especially in the interventional surgery with a long and tortuous intervention pathway, due to the flexibility of the flexible sleeve, the flexible sleeve often moves to the proximal end relative to the guide tube, so that the distal end of the guide tube extends beyond the distal end of the flexible sleeve, thus damaging the surrounding tissues passed by.

In order to solve the technical problem, further, in the embodiment of the present disclosure, the distal end of the flexible sleeve 132 may be subject to shrinkage molding to form a shrunk portion 1321 which can be conical, and the inner diameter of the shrunk portion after being molded may be smaller than the outer diameter of the guide tube 131 of 0.05 mm to 1 mm. FIG. 18 is a schematic diagram of a flexible sleeve formed by shrinking a distal end according to an embodiment of the present disclosure.

Because the inner diameter of the distal end formed by the shrunk portion of the flexible sleeve 132 is smaller than the outer diameter of the distal end of the guide tube 131, in the process of the catheter instrument 13 reaching the puncture target through the intervention pathway, even if the flexible sleeve 132 is subjected to the resistance from the tissues and organs it passes by, the flexible sleeve 132 will not move to the proximal end relative to the guide tube 131, such that the guide tube 131 will not protrude from the distal end of the flexible sleeve 632, thereby harming the tissues passed by.

Figure 19:
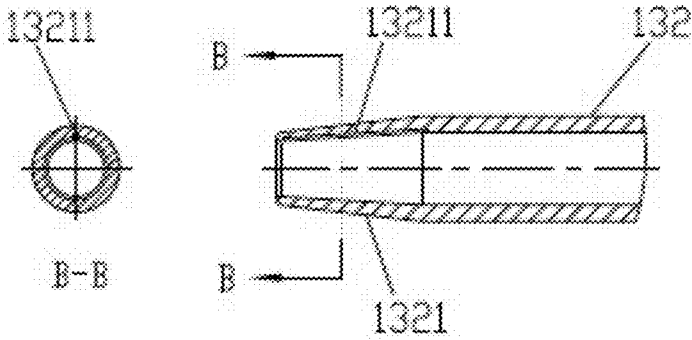
FIG. 19 is a schematic diagram of a shrunk portion of a flexible sleeve according to an embodiment of the present disclosure.

Further, FIG. 19 is a schematic diagram of a shrunk portion of a flexible sleeve according to an embodiment of the present disclosure. In the embodiment of the present disclosure, the shrunk portion 1321 of the flexible sleeve 132 may be provided with a weakened portion 13211 which is easy to be damaged, as shown in FIG. 19. The weakened portion 13211 may extend to the distal opening of the flexible sleeve 132. The weakened portion 13211 may be an intermittent indent line or indentation which may extend to the distal opening of the flexible sleeve 132 in a longitudinal direction of the flexible sleeve 132 in a straight manner or helical manner. The weakened portion 13211 may be provided on the inner surface of the shrunk portion 1321 or the outer surface of the shrunk portion 1321. When the weakened portion 13211 is provided on the outer surface of the shrunk portion 1321, a recess may be formed on the outer surface, which may stimulate the blood vessel wall and also affect the blood flow, thus increasing the possibility of thrombosis. Thus, exemplarily, the weakened portion 13211 is provided on the inner surface of the shrunk portion 1321.

The weakened portion 13211 makes it possible for the guide tube 131 to destroy the weakened portion 1321 and to extend out of the distal opening of the flexible sleeve 132, when the catheter instrument 13 abuts against the puncture target and exerts an acting force greater than the above resistance and pushes the guide tube 131 towards the distal end relative to the flexible sleeve 132. In an embodiment of the present disclosure, the weakened portion 1321 is a longitudinal indentation with 1 mm wide.

Figure 20:
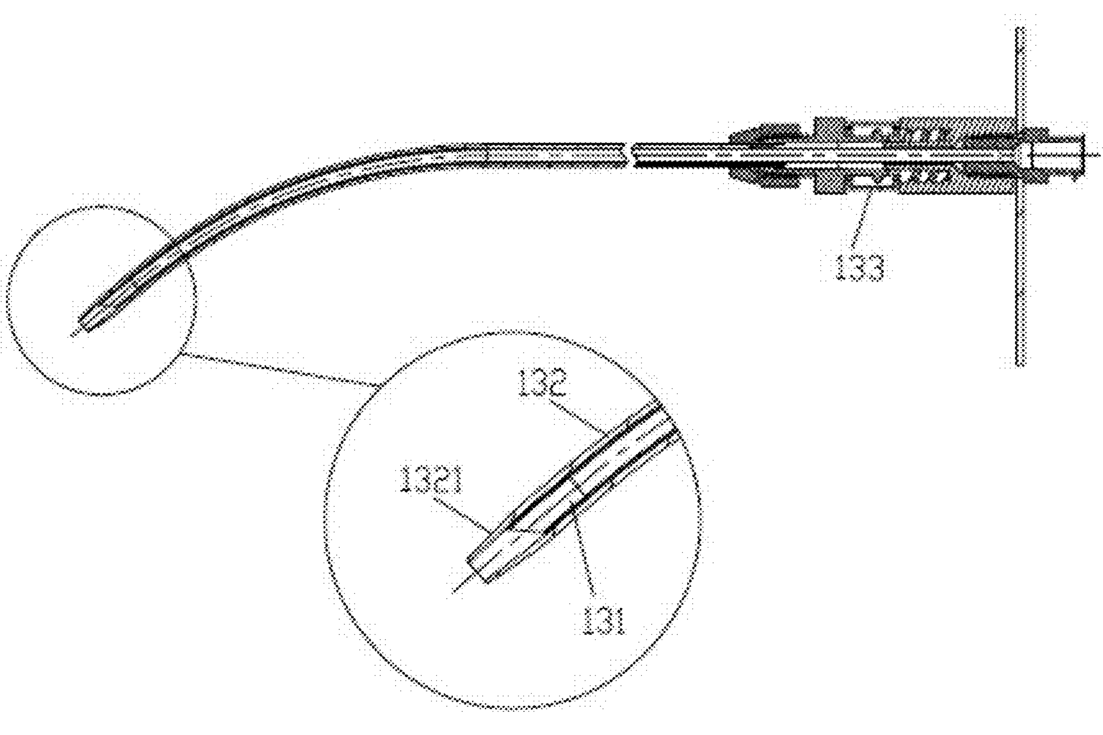
FIG. 20 is a state schematic diagram of the guide tube and flexible sleeve in the process of reaching a puncture target through an intervention pathway according to an embodiment of the present disclosure.

Thus, in the puncture surgery according to the embodiment of the present disclosure, the guide tube 131 and the flexible sleeve 132 first enters the body via the intervention pathway through the skin or the organ cavity canals or the like to reach the puncture target. FIG. 20 is a state schematic diagram of the guide tube and flexible sleeve in the process of reaching a puncture target through an intervention pathway according to an embodiment of the present disclosure. As shown in FIG. 20, in this process, the flexible sleeve 132 sleeves outside the guide tube 131, and the shrunk portion of the flexible sleeve 132 extends 2 mm to 3 mm beyond the distal oblique blade of the guide tube 131 to prevent the distal oblique blade from harming the tissue passed by.

Figure 21:
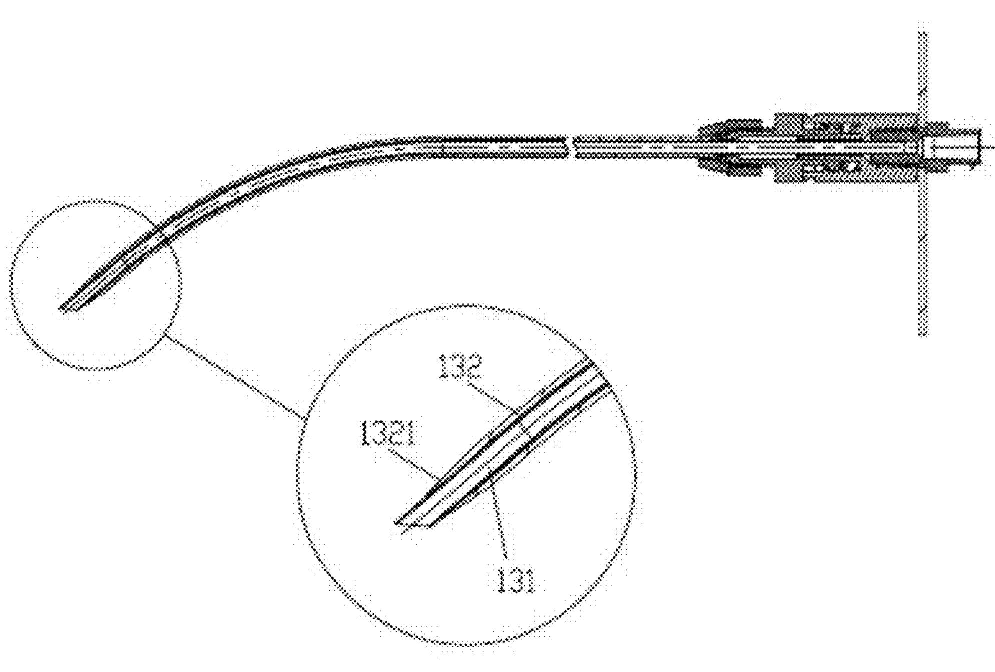
FIG. 21 is a state schematic diagram of the guide tube and the flexible sleeve when implementing puncture guidance according to an embodiment of the present disclosure.

In the puncture surgery according to the embodiment of the disclosure, when the distal end of the catheter instrument 13 reaches the puncture target, an acting force greater than the above resistance can be exerted and the guide tube 131 can be pushed towards the distal end relative to the flexible sleeve 132, so that the guide tube 131 destroys the weakened portion 1321 and extends 2 mm to 3 mm beyond the distal opening of the flexible sleeve 132. Thus, the distal oblique blade of the guide tube 131 can be penetrated into the puncture target, so that the distal oblique blade can always remain at the puncture target during the puncture process to provide puncture guidance for the puncture needle 11. Then the puncture needle 11 passes through the catheter instrument 13 to puncture to the puncture target. FIG. 21 is a state schematic diagram of the guide tube and the flexible sleeve when implementing puncture guidance according to an embodiment of the present disclosure.

Figure 22:
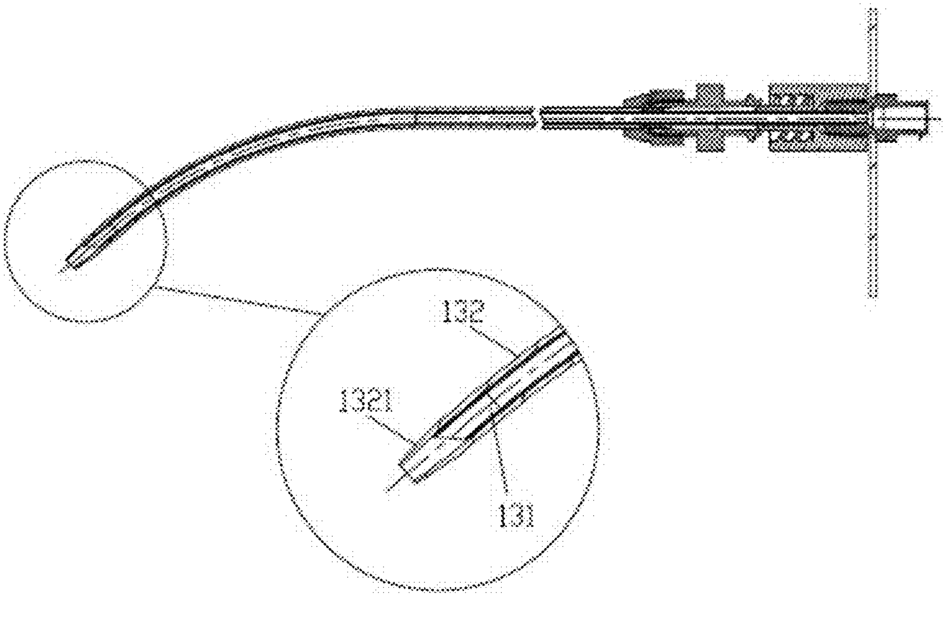
FIG. 22 is a state schematic diagram of the guide tube and flexible sleeve in the exiting process through the intervention pathway after puncture guidance according to an embodiment of the present disclosure.

In the embodiment of the present disclosure, when the puncture by the puncture needle 11 is completed, the guide tube 131 can be pulled back to the proximal end relative to the flexible sleeve 132, so that the distal oblique blade of the guide tube 131 is retracted 3 mm to 5 mm within the distal opening of the flexible sleeve 132. Thereafter, the guide tube 131 and the flexible sleeve 132 are taken out from the original intervention pathway. Since the distal oblique blade of the guide tube 131 has been retracted into the distal opening of the flexible sleeve 132, it will not cause damage to the tissues passed by. In addition, during the withdrawal of the catheter instrument 13, the direction of the resistance exerted on the flexible sleeve 132 is towards the distal end, which will not cause the flexible sleeve 132 to move to the proximal end relative to the guide tube 131, and will not cause the distal end of the guide tube 131 to extend beyond the distal end of the flexible sleeve 132 to cause damage to the tissues passed by. FIG. 22 is a state schematic diagram of the guide tube and flexible sleeve in the exiting process through the intervention pathway after puncture guidance according to an embodiment of the present disclosure.

The interventional catheter instrument according to the embodiment of the disclosure can not only prevent damage to the surrounding tissues the interventional catheter instrument passes, but also be kept at the interventional target in the blood vessel or tissues during the intervention process, so as to build a stable and reliable guiding structure for the surgeon to guide the puncture or insert the interventional instrument. The interventional catheter instrument has the advantages of simple structure and process, low cost, good operability, high efficiency and safety, and can meet the requirements of the surgeons for accurate guidance in curved puncture.

The puncture instrument according to the embodiment of the present disclosure can operate a puncture surgery that is easier to operate, more accurate and effective, safer under the interventional navigation technology, thus solving the technical problems existing in the prior art.

In summary, the above embodiments describe the puncture instrument in detail. Of course, the present disclosure includes but is not limited to the above embodiments, and any content transformed on the basis of the above embodiments falls within the scope protected by the disclosure. Those skilled in the art may draw inferences from the contents of the above embodiments.

The above description is only description of a better embodiment of the disclosure, not any limitation to the scope of the disclosure, and any changes and modifications made by those ordinarily skilled in the technical field where the present disclosure belongs according to the above disclosed contents all fall within the scope of protection of the claims.

Although the disclosure is described with reference to the exemplary embodiments, it should be understood that the disclosure is not limited to the specific embodiments described and shown in detail herein, and that those skilled in the art may make various changes to the exemplary embodiments without deviating from the scope defined in the claims, all such changes falling within the scope of protection of the present disclosure.

Although exemplary embodiments of the present disclosure have been described, additional changes and modifications may be made to these embodiments once the basic creative concepts are known to those skilled in the art. Accordingly, the attached claims are intended to be construed to include exemplary embodiments and all changes and modifications falling within the scope of the present disclosure.

Obviously, those skilled in the art may make various changes and modifications of the present disclosure without deviating from the spirit and scope of the present disclosure. Thus, if the various equivalent changes or modifications of the present disclosure are made within the scope of the disclosure and the equivalent technology, the present disclosure intends to include the equivalent changes or modifications.

Although the disclosure is described with reference to the exemplary embodiments, it should be understood that the disclosure is not limited to the specific embodiments described and shown in detail herein, and that those skilled in the art may make various changes to the exemplary embodiments without deviating from the scope defined in the claims, all such changes falling within the scope of protection of the disclosure.

Although preferred embodiments of the disclosure have been described, additional changes and modifications may be made to these embodiments once the basic creative concepts are known to those skilled in the art. Accordingly, the attached claims are intended to be construed to include preferred embodiments and all changes and modifications falling within the scope of the disclosure.

Obviously, those skilled in the art may make various changes and modifications of the present disclosure without deviating from the spirit and scope of the present disclosure. Thus, if the various equivalent changes or modifications of the present disclosure are made within the scope of the disclosure and the equivalent technology, the present disclosure intends to include the equivalent changes or modifications.

What is claimed is:

1. A puncture instrument, comprising:

a puncture needle which comprises a sensor mounting portion capable of mounting an electromagnetic sensor, wherein the puncture instrument comprises an interventional catheter instrument, which comprises:

a guide tube; and a flexible sleeve which sleeves outside the guide tube;

wherein the flexible sleeve and the guide tube are capable of moving relatively to each other so that a distal end of the flexible sleeve extends beyond a distal end of the guide tube, or the distal end of the guide tube extends beyond the distal end of the flexible sleeve, wherein the distal end of the flexible sleeve is provided with a shrunk portion, an inner diameter of the shrunk portion is smaller than an outer diameter of the guide tube, and the shrunk portion is provided with a weakened portion which is easy to be damaged; when the interventional catheter instrument abuts against a puncture target, the weakened portion is capable of being destroyed by causing the guide tube to move to the distal end relative to the flexible sleeve, so that the guide tube extends beyond the distal end of the flexible sleeve;

wherein the weakened portion extends to a distal opening of the flexible sleeve; and wherein the weakened portion is provided on an inner surface or an outer surface of the shrunk portion.

2. The puncture instrument according to claim 1, wherein the sensor mounting portion is an internal cavity of the puncture needle or a concave portion of body surface of the puncture needle.

3. The puncture instrument according to claim 1, wherein the puncture needle is tubular, one end of a tubular cavity of the puncture needle is opened at a proximal end of the puncture needle, the other end of the tubular cavity is closed at a distal end of the puncture needle, and the tubular cavity forms the sensor mounting portion.

4. The puncture instrument according to claim 1, wherein the puncture needle comprises a needle head and a needle rod, and the needle head and the needle rod are connected by welding or threading;

wherein a proximal end of the needle head comprises a connection portion, the needle rod is tubular, and when the needle head is connected with the needle rod, the connection portion is inserted into a tubular cavity of the needle rod.

5. The puncture instrument according to claim 1, wherein an outer diameter of a distal portion of a needle rod of the puncture needle is smaller than an outer diameter of a proximal portion of the needle rod.

6. The puncture instrument according to claim 1, wherein a needle rod of the puncture needle includes an inner needle rod and an outer needle rod, and the outer needle rod sleeves outside the inner needle rod, and the outer needle rod is connected with the inner needle rod by welding.

7. The puncture instrument according to claim 6, wherein the inner needle rod and the outer needle rod are sealed by welding or bonding.

8. The puncture instrument according to claim 6, wherein at a distal portion of the needle rod, the inner needle rod extends beyond the outer needle rod.

9. The puncture instrument according to claim 1, wherein the puncture needle comprises an auxiliary portion, the auxiliary portion sleeves outside a needle rod of the puncture needle, and a friction coefficient of the auxiliary portion is smaller than that of the needle rod.

10. The puncture instrument according to claim 9, wherein the auxiliary portion is a spring or a sleeve; and an outer diameter of a distal portion of the needle rod is smaller than an outer diameter of a proximal portion of the needle rod, and the spring or the sleeve sleeves at the distal portion of the needle rod.

11. The puncture instrument according to claim 9, wherein the needle rod comprises an outer needle rod and an inner needle rod; wherein the auxiliary portion is a spring or a sleeve; and the outer needle rod comprises a distal outer needle rod and a proximal outer needle rod, the distal outer needle rod sleeves at a distal end of the inner needle rod, the proximal outer needle rod sleeves at a proximal end of the inner needle rod, and the spring or the sleeve sleeves outside the inner needle rod between the distal outer needle rod and the proximal outer needle rod.

12. The puncture instrument according to claim 9, wherein the needle rod comprises an outer needle rod and an inner needle rod; wherein the auxiliary portion is a spring or a sleeve; and an outer diameter of a distal portion of the inner needle rod is smaller than an outer diameter of a proximal portion of the inner needle rod, and the outer needle rod and the spring sequentially sleeve at the distal portion of the inner needle rod from a distal end of the inner needle rod to a proximal end of the inner needle rod, or the outer needle rod and the sleeve sequentially sleeve at the distal portion of the inner needle rod from the distal end to the proximal end.

13. The puncture instrument according to claim 9, wherein the needle rod comprises an outer needle rod and an inner needle rod; wherein the auxiliary portion is a spring or a sleeve; and at a distal portion of the needle rod, the inner needle rod extends beyond the outer needle rod, and the spring or the sleeve sleeves at a portion of the inner needle rod that extends beyond the outer needle rod.

14. The puncture instrument according to claim 1, wherein the inner diameter of the shrank portion is smaller than the outer diameter of the guide tube by 0.05 mm to 1 mm.

15. The puncture instrument according to claim 1, wherein a thickness specification of the guide tube comprises: 13 G, 14 G, 15 G, and 16 G, and a length of the guide tube is 42 cm to 57 cm.

16. The puncture instrument according to claim 1, wherein an inner diameter of the flexible sleeve is greater than an outer diameter of the guide tube by 0.1 mm to 2 mm.

17. The puncture instrument according to claim 1, wherein the interventional catheter instrument comprises a connector through which a proximal end of the guide tube is connected with a proximal end of the flexible sleeve, and the guide tube and the flexible sleeve are able to move relative to each other through the connector.

18. The puncture instrument according to claim 17, wherein a connection method of the connector comprises threaded connection, clasping connection or bonding connection.

* * * * *